(12) United States Patent
Schmidt (10) Patent No.: US 11,653,844 B2
(45) Date of Patent: May 23, 2023

(54) RISK DETERMINATION OF CORONARY ARTERY DISEASE

(71) Applicant: ACARIX A/S, Kgs Lyngby (DK)

(72) Inventor: Samuel Emil Schmidt, Aalborg (DK)

(73) Assignee: ACARIX A/S, Kgs Lyngby (DK)

( * ) Notice: Subject to any disclaimer, the term of this patent is extended or adjusted under 35 U.S.C. 154(b) by 260 days.

(21) Appl. No.: 16/759,038

(22) PCT Filed: Oct. 25, 2018

(86) PCT No.: PCT/EP2018/079263
§ 371 (c)(1),
(2) Date: Apr. 24, 2020

(87) PCT Pub. No.: WO2019/081630
PCT Pub. Date: May 2, 2019

(65) Prior Publication Data
US 2020/0367771 A1    Nov. 26, 2020

(30) Foreign Application Priority Data

Oct. 26, 2017 (EP) ..................... 17198552

(51) Int. Cl.
*A61B 5/024* (2006.01)
*A61B 5/0255* (2006.01)
(Continued)

(52) U.S. Cl.
CPC ........ *A61B 5/02405* (2013.01); *A61B 5/0255* (2013.01); *A61B 5/7275* (2013.01); *A61B 7/045* (2013.01)

(58) Field of Classification Search
CPC . A61B 5/02405; A61B 5/0255; A61B 5/7275; A61B 7/045; A61B 7/00
See application file for complete search history.

(56) References Cited

U.S. PATENT DOCUMENTS 10,182,735 B2    1/2019   Thakur et al.
2007/0265533 A1  11/2007  Tran
(Continued)

FOREIGN PATENT DOCUMENTS

CN    1850007     10/2006
CN    107249466   10/2017
(Continued)

OTHER PUBLICATIONS

International Search Report on corresponding PCT application (PCT/EP2018/079263) from International Searching Authority (EPO) dated Dec. 19, 2018.
(Continued)

*Primary Examiner* — Paula J Stice
(74) *Attorney, Agent, or Firm* — Kos IP Law LLP (57) ABSTRACT

The proposed technology relates to a method for indicating a risk for coronary artery disease. A sound recording is obtained (100) covering a plurality of heartbeats, a plurality of heart sounds are identified (200) in the sound recording, and a plurality of segments are obtained (300) from the sound recording. A frequency power measure is determined (400) based on the signal strength of a first frequency window of a period in the diastole, an amplitude of the fourth heart sound is determined (500) based on the plurality of heart sounds and the plurality of segments, and an indication of a heart rate variability is determined (600) based on the plurality of heart sounds. The indication of the risk for coronary artery disease is then determined (700) based on the frequency power measure, the amplitude of the fourth heart sound, and the indication of the heart rate variability.

18 Claims, 4 Drawing Sheets

(51) Int. Cl.
*A61B 5/00* (2006.01)
*A61B 7/04* (2006.01)

(56) References Cited

U.S. PATENT DOCUMENTS

| | | |
|---|---|---|
| 2008/0228094 A1 | 9/2008 | Audet |
| 2010/0023081 A1 | 1/2010 | Audet et al. |
| 2010/0113954 A1 | 5/2010 | Zhou |
| 2014/0180153 A1 | 6/2014 | Zia et al. |
| 2014/0296726 A1 | 10/2014 | Brockway et al. |
| 2015/0157273 A1 | 6/2015 | An |

FOREIGN PATENT DOCUMENTS

| | | |
|---|---|---|
| CN | 108471968 | 8/2018 |
| EP | 2462871 | 6/2012 |
| WO | 2016034907 | 3/2016 |
| WO | WO2016162503 | 10/2016 |

OTHER PUBLICATIONS

Written Opinion on corresponding PCT application (PCT/EP2018/079263) from International Searching Authority (EPO) dated Dec. 19, 2018.

Winther et al.; "Diagnosing coronary artery disease by sound analysis from coronary stenosis induced turbulent blood flow: diagnostic performance in patients with stable angina pectoris"; International Journal of cardiovascular imaging Kluwer academic publishers; Dordrecht, NL; vol. 32, No. 2; Sep. 3, 2015; XP035902895.

Schmidt et al.; "Acoustic features for the identification of coronary artery disease"; IEEE transactions on biomedical engineering; IEEE service center, Piscataway, NJ, USA; vol. 62, No. 11; Nov. 1, 2015; XP011587175.

Yusaku Sakakibara, et al. Decrease in the Respiratory Component of the Heart Rate Variability Spectrum in Coronary Artery Disease: Non-Invasive Indicator of Coronary Arteriosclerosis Severity, Electrocardiogram, Japan, 1989, vol. 9, No. 1, pp. 133-139, DOI: https://doi.org/10.5105/jse.9.133.

Fig. 1

100 - obtaining sound recording covering a plurality of heartbeats

200 - identifying plurality of heart sounds in sound recording

300 - obtaining plurality of segments from the sound recording

400 - determining frequency power measure (FPM)

500 - determining amplitude of the fourth heart sound (S4Amp)

600 - determining indication of a heart rate variability (HRV)

700 - determining indication of CAD based on FPM, S4Amp, and HRV

Fig. 2

300 - obtaining plurality of segments from sound recording

302 - dividing sound recording based on first specific heart sounds (SS1)

Fig. 3

400 - determining frequency power measure (FPM)

402 - determining position in time of period in diastole

404 - determining position in time of second heart sound (S2)

406 - determining period in diastole realitve to S2

408 - determining first sum of energy in first frequency window of period

410 - determining second sum of energy in second freq. window of period

412 - determining FPR based on ratio between first and second sum

Fig. 4

```
500 - determining amplitude of fourth heart sound (S4Amp)
  502 - aligning segments
  504 - calculating mean segment
  506 - determining S4Amp based on the energy of mean segment
    508 - determ. pos. in time of first heart sound (S1) in mean segment
    510 - determining fourth heart sound (S4) period in mean segment
    512 - determining energy of the fourth heart sound (S4) period
```

Fig. 5

```
600 - determining indication of heart rate variability (HRV)
  602 - determining pos. in time for fourth specific heart sounds (SS4)
  604 - determining heart beat durations (HBD) based on pos. in time
  606 - determ. HRV based on the variation of heart beat durations (HBD)
```

Fig. 6a

600 - determining indication of heart rate variability (HRV)

610 - determ. signal str. of third freq. window covering pl. of heartbeats

612 - determ. signal str. of fourth freq. window covering pl. of heartbeats

614 - determining indication of HRV based on the signal strengths

RISK DETERMINATION OF CORONARY ARTERY DISEASE

CROSS-REFERENCE TO RELATED APPLICATION

This application is the National Phase, under 35 U.S.C. § 371(c), of International Application No. PCT/EP2018/079263, filed Oct. 25, 2018, which claims priority from EP 17198552.6, filed Oct. 26, 2017. The disclosures of all of the referenced applications are incorporated herein by reference in their entirety.

FEDERALLY SPONSORED RESEARCH OR DEVELOPMENT

Not Applicable

TECHNICAL FIELD

The proposed technology generally relates to the field of diagnosing suspected coronary artery disease (CAD), and in particular to devices or apparatuses for indicating a risk for coronary artery disease (CAD) that are non-invasive.

BACKGROUND

Diagnosing suspected coronary artery disease (CAD) requires substantial health care resources. Invasive coronary angiography (ICA) is commonly used today, but is costly and carries the risk of complications. There are non-invasive technologies available for diagnosing CAD. For example, recent advances in sound sensor technology, analytic power, and data filtering have enabled the use of acoustic detection to diagnose intracoronary turbulence due to obstructive CAD. Such acoustic based technologies are non-invasive, radiation-free, and economically favorable. Typically, these can be used for primary risk stratification of a low-to-intermediate risk population. Improvement in the accuracy of these technologies is therefore highly relevant in daily clinical practice.

OBJECT

The proposed technology aims at meeting the above described need, and in particular at improving diagnostic accuracy of acoustic based technologies for diagnosing suspected CAD.

SUMMARY

In a first aspect of the proposed technology at least the primary object is attained by a method for indicating a risk for coronary artery disease (CAD) for a person. The method comprises: obtaining a sound recording covering a plurality of heartbeats; identifying a plurality of heart sounds (S) in the sound recording; and obtaining a plurality of segments from the sound recording based on the plurality of heart sounds (S), wherein each segment covers at least a portion of a heart cycle. The method further comprises: determining a frequency power measure (FPM) based on the signal strength of a first frequency window of a period in the diastole of a first number of segments of the plurality of segments; and determining an amplitude of the fourth heart sound (S4Amp) based on the plurality of heart sounds (S) and the plurality of segments.

Here, the signal strength of the first frequency window is understood to encompass the amplitudes in, or energy of the first frequency window, and the period in the diastole is understood to encompass an interval in the diastole. The method further comprises: determining the indication of the risk for coronary artery disease (CAD) based on the frequency power measure (FPM) and the amplitude of the fourth heart sound (S4Amp). The method may further comprise: determining an indication of a heart rate variability (HRV) based on the plurality of heart sounds (S), and determining the indication of the risk for coronary artery disease (CAD) may further be based on the indication of the heart rate variability (HRV).

The method according to the first aspect of the proposed technology may be performed by an electronic stethoscope or a system for indicating a risk for coronary artery disease (CAD). The sound recording may be obtained by a microphone and the remaining or other steps may be performed by a processor.

According to a second aspect, the above objects are achieved by a system for indicating a risk for coronary artery disease (CAD) for a person. The system comprises: a microphone configured to be placed on the chest of the person for obtaining sounds from the heart of the person; and a processor operatively connected to the microphone and configured to perform the method according the first aspect.

According to a second aspect, the above objects are achieved by a computer program product for being used in a system comprising: a microphone configured to be placed on the chest of the person for obtaining sounds from the heart of the person and a processor operatively connected to the microphone. The computer program product comprises program code instructions configured to, when executed by the processor of the system, cause the processor to perform the method according to the first aspect.

Here, a microphone is understood to encompass a transducer suitable for obtaining sound recordings.

In an alternative to the proposed technology, only one of the frequency power measure (FPM) and the amplitude of the fourth heart sound (S4Amp) is determined and used in the determining of the indication of the risk for coronary artery disease (CAD). For example, determining the indication of the risk for coronary artery disease (CAD) may be based on the frequency power measure (FPM) or the amplitude of the fourth heart sound (S4Amp), and on the indication of the heart rate variability (HRV).

A number of features that relate to the segmentation of the sound recording have been found to be advantageous to the proposed technology.

The plurality of heart sounds (S) may comprise a plurality of first specific heart sounds (SS1), and obtaining a plurality of segments from the sound recording may comprise: dividing the sound recording into the plurality of segments based on the plurality of first specific heart sounds (SS1). Each segment may cover a complete heart cycle.

The plurality of first specific heart sounds (SS1) may comprise second heart sounds (S2), each relating to the aortic valve closure (AC). The plurality of segments may comprise a first number of segments, each covering at least the second heart sound (S2) and the subsequent diastole of a single heartbeat. The plurality of first specific heart sounds (SS1) may comprise first heart sounds (S1), each relating to the mitral valve closure (MC). The plurality of segments may comprise a second number of segments, each covering at least the fourth heart sound (S4) relating to the elastic limit of the distending of the ventricular wall and the subsequent first heart sound (S1) of a single heartbeat.

A number of features that relate to the frequency power measure (FPM) have been found to be advantageous and contributing to an improved accuracy of the proposed technology.

The step of determining a frequency power measure (FPM) may further be based on the signal strength of a second frequency window of the period, or interval in the diastole of each segment, wherein the second frequency window has a low cutoff that is above a high cutoff of the first frequency window. Here, the signal strength of the second frequency window is understood to encompass the amplitudes in, or energy of, the second frequency window. The step of determining the frequency power measure (FPM) may further comprise: determining a first sum based on the sum of the energy in the first frequency window of the first number of segments; and determining a second sum based on the sum of the energy in the second frequency window of the first number of segments. Here, a sum is understood to encompass a mean. The determining of the frequency power measure (FPM) may then be based on a ratio (FPR) between, or the relative magnitude of, the first sum and the second sum.

The first frequency window may have a low cutoff in the range 20-40 Hz, or at 30 Hz. Additionally or alternatively, the first frequency window may have a high cutoff in the range 80-100 Hz, or at 90 Hz. The second frequency window may have a low cutoff in the range 180-220 Hz, or at 200 Hz. Additionally or alternatively, the second frequency window may have a high cutoff in the range 250-800 Hz, 280-320 Hz, or at 300 Hz.

The plurality of heart sounds (S) may comprise a plurality of second specific heart sounds (SS2), and determining a frequency power measure (FPM) may comprise: determining the position in time of the period in the diastole of each of the first number of segments relative to the second specific heart sound (SS2) in the segment. The second specific heart sound (SS2) may be the second heart sound (S2) relating to the aortic valve closure (AC). The position in time of the second heart sound (S2) may correspond to the onset, or the peak, of the of the second heart sound (S2).

The step of determining the position in time of the period, or interval, may comprise: determining the position in time of the second heart sound (S2) in each of the first number of segments; and determining the period, or interval, in the diastole in each segment as a period, or interval, that starts after 160-190 milliseconds, or after 175 milliseconds, after to the position in time of the second heart sound (S2) of the segment and ends before 430-470 milliseconds, or before 450 milliseconds, after to the position in time of the second heart sound (S2) of the segment.

A number of features that relate to the amplitude of the fourth heart sound (S4Amp) have been found to be advantageous and contributing to an improved accuracy of the proposed technology.

The plurality of heart sounds (S) may comprise a plurality of third specific heart sounds (SS3), and the step of determining an amplitude of the fourth heart sound (S4Amp) may comprise: aligning a second number of segments of the plurality of segments based on the plurality of third specific heart sounds (SS3); calculating a mean segment based on the aligned second number of segments; and determining the amplitude of the fourth heart sound (S4Amp) based on the energy of the fourth heart sound (S4) in the mean segment. Here, a mean segment is understood to encompass a sum of segments, and the energy of the fourth heart sound (S4) is understood to encompass the signal strength at, or peak amplitude of, the fourth heart sound (S4).

The third specific heart sound (SS3) may be the first heart sound (S1) relating to the mitral valve closure (MC). The step of determining the amplitude of the fourth heart sound (S4Amp) may comprise: determining the position in time of the first heart sound (S1) in the mean segment; determining a fourth heart sound period, or interval, in the mean segment that starts in the range 100-140 milliseconds, or at 120 milliseconds, before the position in time of the first heart sound (S1) and ends in the range 20-10 milliseconds, or at 15 milliseconds, before the position in time of the first heart sound (S1); and determining the amplitude of the fourth heart sound (S4Amp) based on the energy of, or the signal strength at, or peak amplitude of, fourth heart sound period, or interval. Here, the energy of the fourth heart sound period, or interval, is understood to encompass the signal strength at, or peak amplitude of the fourth heart sound period.

The position in time of the first heart sound (S1) may correspond to the onset, or the peak, of the of the first heart sound (S1).

Two different approaches to determining the indication of the heart rate variability (HRV) have been found to be advantageous and contributing to an improved accuracy of the proposed technology.

In the first approach, the step of determining the indication of the heart rate variability (HRV) may comprise: determining the positions in time for a plurality of fourth specific heart sounds (SS4) of the plurality of heart sounds (S); determining a plurality of heart beat durations (HBD), wherein each heart beat duration (HBD) is the time, or difference, between the positions in time of two consecutive fourth specific heart sounds (SS4); and determining the indication of the heart rate variability (HRV) based on the variation of the plurality of heart beat durations (HBD). Here the variation of the plurality of heart beat durations (HBD) is understood to encompass the dispersion, or standard deviation, of the plurality of heart beat durations (HBD).

The position in time of a fourth specific heart sound (SS4) of the plurality of fourth specific heart sounds (SS4) may correspond to the onset, or the peak of, the fourth specific heart sound (SS4). Each of the plurality of fourth specific heart sound (SS4) may be the first heart sound (S1) relating to the mitral valve closure (MC).

In the second approach, the step of determining the indication of the heart rate variability (HRV) may comprise: determining the signal strength of a third frequency window of a period, or interval, of the sound recording covering at least a portion of the plurality of heartbeats, wherein the third frequency window has a high cutoff that is below 2 Hz, or below 1 Hz; and determining the indication of the heart rate variability (HRV) based on the signal strength of the third frequency window. Here, the signal strength of the third frequency window is understood to encompass the amplitudes in, or energy of, the third frequency window.

The third frequency window may have a low cutoff that is above 0.001 Hz. Additionally or alternatively, the third frequency window may have a low cutoff in the range 0.001-0.005 Hz, or at 0.003 Hz, and a high cutoff in the range 0.02-0.06, or at 0.04 Hz, or a low cutoff that in range 0.02-0.06 Hz, or at 0.04 Hz, and a high cutoff in the range 0.1-0.2, or at 0.15 Hz, or a low cutoff in the range 0.1-0.2 Hz, or at 0.15 Hz, and a high cutoff in the range 0.3-0.5, or at 0.4 Hz.

The step of determining the indication of the heart rate variability (HRV) may further comprise: determining the signal strength of a fourth frequency window of the period, or interval of the sound recording, wherein the fourth frequency window has a high cutoff that is below 2 Hz, or below 1 Hz, and does not overlap, or partly overlaps, the third frequency window; and determining the indication of the heart rate variability (HRV) may further be based on the signal strength of the fourth frequency window. Here, the signal strength of the fourth frequency window is understood to encompass the amplitudes in, or energy of, the fourth frequency window.

The fourth frequency window has a low cutoff that is above 0.001 Hz. Additionally or alternatively, the fourth frequency window may have a low cutoff that in range 0.001-0.005 Hz, or at 0.003 Hz, and a high cutoff in the range 0.02-0.06, or at 0.04 Hz, or a low cutoff in the range 0.02-0.06 Hz, or at 0.04 Hz, and a high cutoff in the range 0.1-0.2, or at 0.15 Hz, or a low cutoff in the range 0.1-0.2 Hz, or at 0.15 Hz, and a high cutoff in the range 0.3-0.5, or at 0.4 Hz.

An advantageous approach to determine the actual risk indicator has been identified. The step of determining an indication of the risk for coronary artery disease (CAD) may further based on a trained linear discriminate analysis (LDA) involving the frequency power measure (FPM) and the amplitude of the fourth heart sound (S4Amp). The trained linear discriminate analysis (LDA) may further involve the indication of the heart rate variability (HRV).

Further advantages with and features of the proposed technology will be apparent from the following detailed description of an embodiment.

BRIEF DESCRIPTION OF THE DRAWINGS

A more complete understanding of the abovementioned and other features and advantages of the proposed technology will be apparent from the following description of embodiments in conjunction with the appended drawings, wherein.

DETAILED DESCRIPTION

Figure 1:
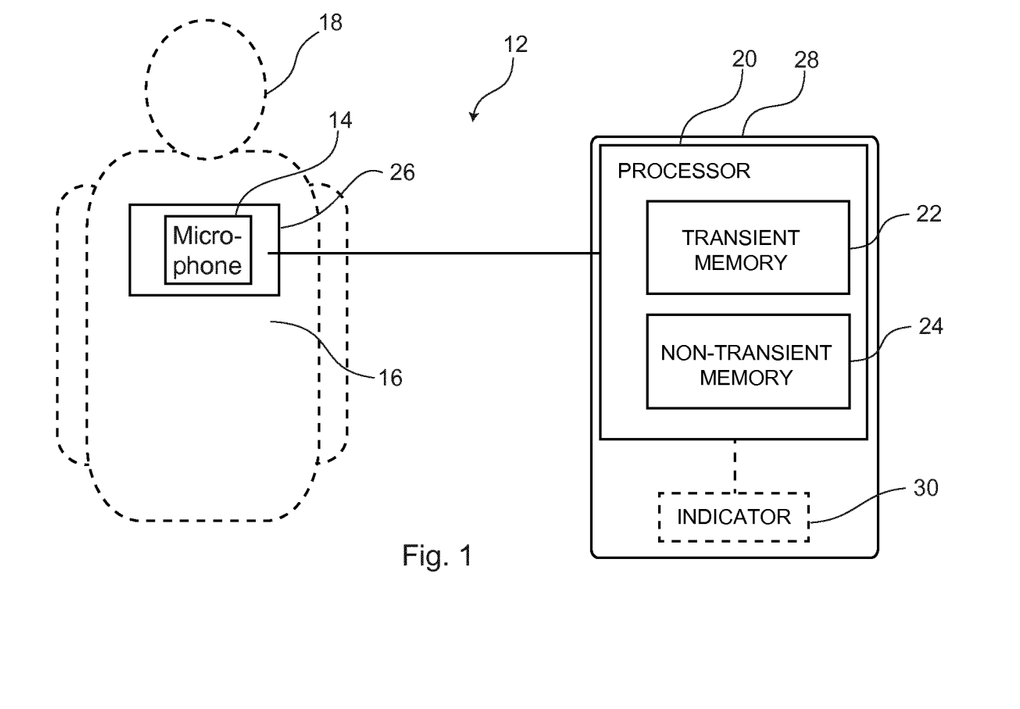
FIG. 1 is a schematic view of an embodiment of the proposed system.

FIG. 1 schematically illustrates an embodiment of a system 12 for indicating a risk for coronary artery disease (CAD) for a person 18. The system 12 has a microphone 14 that can be placed on the chest 16 of a person 18 for obtaining sounds from the heart of the person 18. A processor 20 is connected to the microphone 14. The processor 20 has a transient memory 22 which can store a signal received from the microphone 14, and by which it can execute program code instructions. The system 12 has a support 26 that supports the microphone 14 and a housing 28 that accommodates the processor 20. The system 12 also has a non-transient memory 24 storing program code instructions for the processor 20. For example, the system 12 as a whole can be an integral part of a smart-phone, or all parts except the microphone 14 and the support 26 can form part of a smart-phone. In one embodiment, the microphone 14 is an integrated microphone of a smart-phone.

In one embodiment of the system 12, it additionally has an indicator 30 operatively connected to the processor 20. The indicator 30 can, for example, have an LCD display, or the like, that can display output information from the processor 20 indicating the risk for CAD, such as a number.

Figure 2:
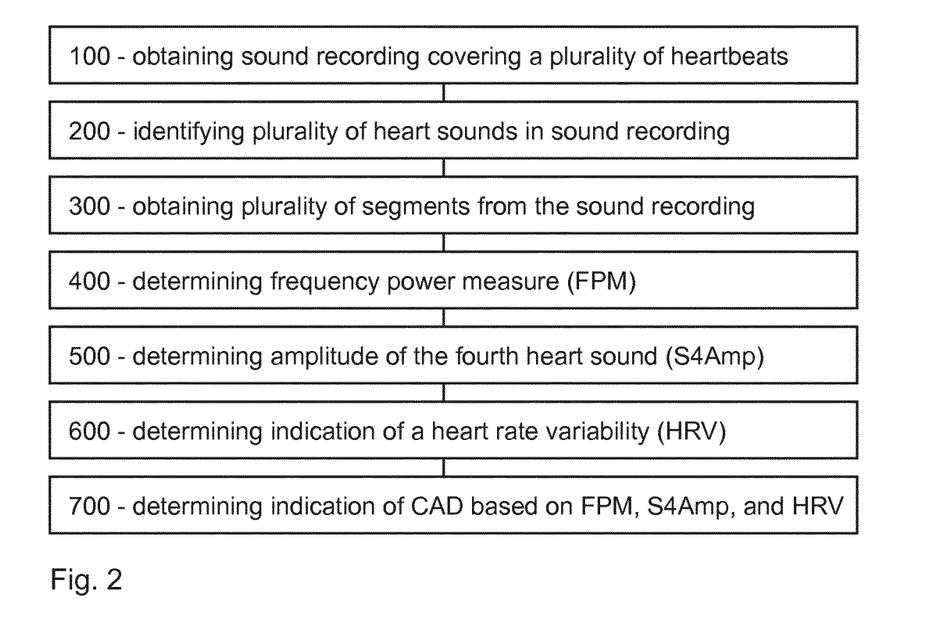
FIG. 2 is a schematic flowchart illustrating an embodiment of the proposed method.

The program code instructions in the non-transient memory 24 cause the processor 20 to perform the method shown in FIG. 2. The microphone 14 is placed on the chest 16 of a person 18 and a signal is recorded. This way, a sound recording covering a plurality of heartbeats recorded by a microphone placed on the chest of the person is obtained 100. In one embodiment, the signal is first stored in a database and subsequently retrieved from the database by the processor.

A plurality of heart sounds (S) is then identified 200 in the sound recording based on a duration-depended hidden Markov model.

Figure 3:
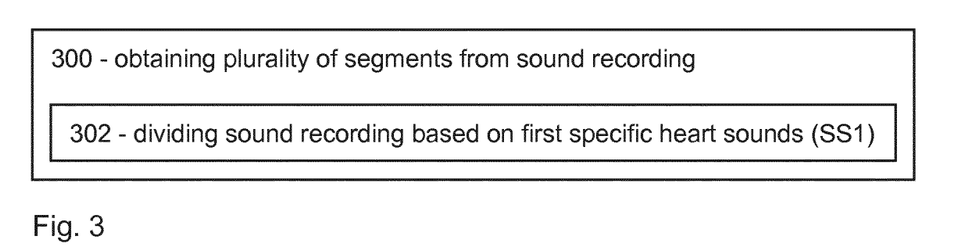
FIG. 3 is a schematic flowchart illustrating an embodiment of a step for obtaining a segmentation.

The plurality of heart sounds (S) contains a plurality of first specific heart sounds (SS1) in the form of first heart sounds (S1) generated by mitral valve closures (MC). A plurality of segments, each covering a portion of a complete heart cycle, are then obtained 300 from the sound recording by dividing 302 the sound recording into the plurality of segments based on the first heart sounds (S1), as is indicated in FIG. 3. The segmentation is performed using a commonly known duration depended hidden Markov model and the plurality of segments includes periods that individually covers the first heart sound (S1), the second heart sound (S2), the diastole, and the systole.

Figure 4:
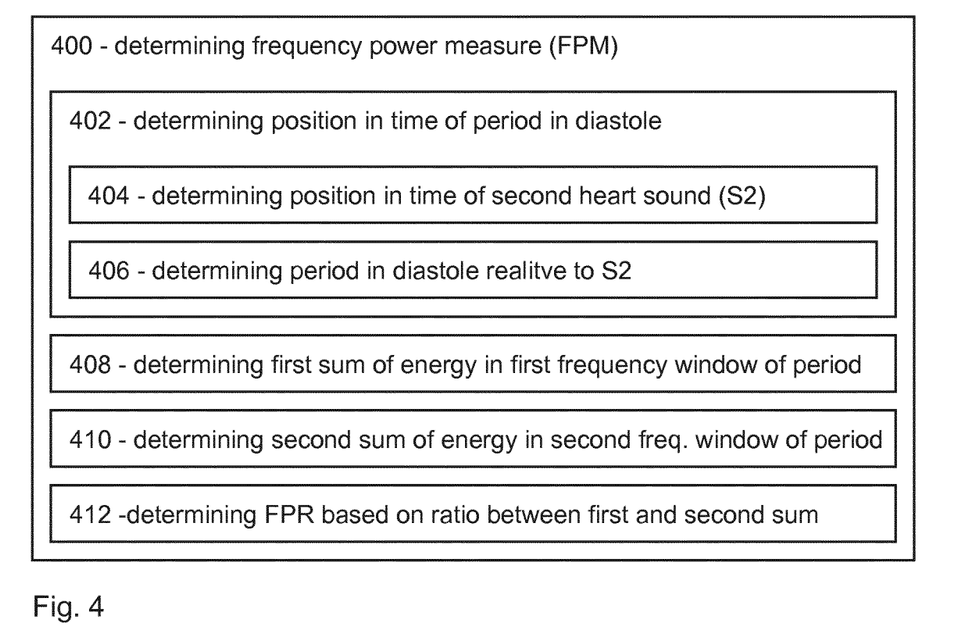
FIG. 4 is a schematic flowchart illustrating an embodiment of a step for determining a frequency power measure (FPM)

In the next step of the method a frequency power measure (FPM) is determined (400), which is illustrated in detail in FIG. 4. The plurality of heart sounds (S) contains a plurality of second specific heart sounds (SS2) in the form of second heart sounds (S2) generated by aortic valve closures (AC). First, the position in time of a period in each of the segments is determined 402. This is done by determining 404 the position in time of the second heart sound (S2) in the segments including the second heart sound (S2), where the position in time is the second heart sound (S2) in each segment. This is followed by determining 406 the period as the interval starting after 175 milliseconds after the position in time of the second heart sound (S2) of the segment, and ending before 450 milliseconds after the position in time of the second heart sound (S2) of the segment. This way, a period in the diastole of each segment has been determined.

A first sum is determined 408 for each segment, where the first sum is the sum of the energy in a first frequency window of abovementioned period of the segment. The first frequency window has a low cutoff at 30 Hz and a high cutoff at 90 Hz. Similarly, a second sum is determined 410 for each segment, where the second sum is the sum of the energy in a second frequency window of abovementioned period of the segment. The second frequency window has a low cutoff at 200 Hz and a high cutoff at 300 Hz. The frequency power measure (FPR) is then determined 412 based on the ratio between the first sum and the second sum.

In one embodiment, the above is achieved by dividing the period into 75% overlapping sub-windows of 128 milliseconds which are subjected to a Fourier transform providing a frequency power spectrum. The square root of the frequency power spectrum is calculated and the mean spectrum for each sub-window is then estimated. A medium spectrum is estimated by calculating the medium spectrum across the segments. The frequency power measure (FPR) is then determined as the ratio between the sum of the amplitudes in the 30-90 Hz band over the sum of the amplitudes in the 200-300 Hz band In summary, the frequency power measure (FPM) is determined 400 based on the signal strengths of a first frequency window and a second frequency window of a period in the diastole, where the second frequency window has a low cutoff that is above a high cutoff of the first frequency window.

Figure 5:
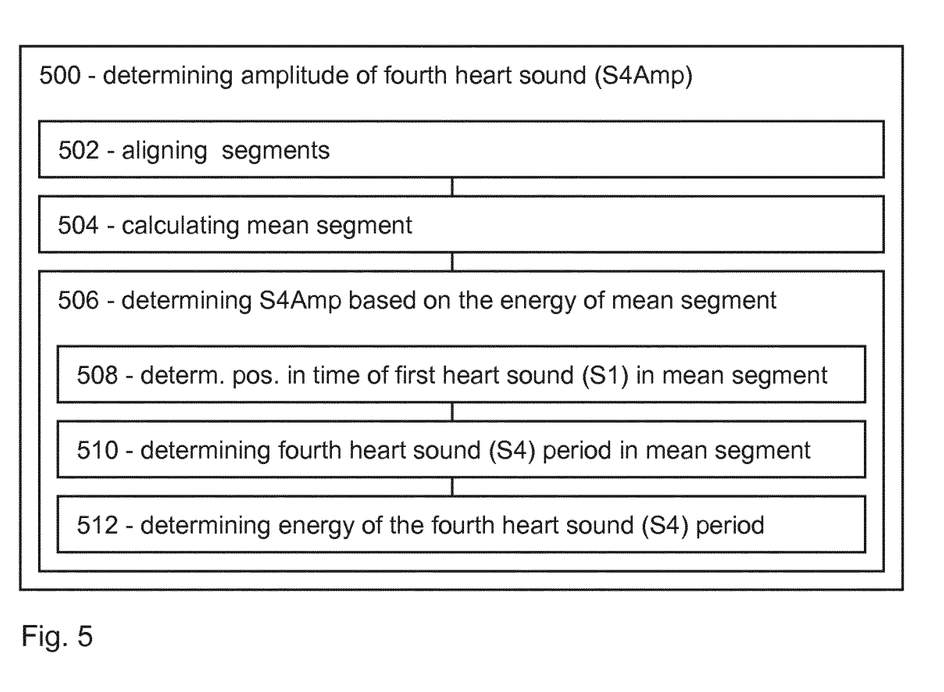
FIG. 5 is a schematic flowchart illustrating an embodiment of a step for determining an amplitude of the fourth heart sound (S4Amp)

In the next step of the method the amplitude of the fourth heart sound (S4Amp) is determined 500, which is illustrated in detail in FIG. 5. The plurality of heart sounds (S) contains a plurality of third specific heart sounds (SS3) in the form of first heart sounds (S1) generated by mitral valve closures (MC). The segments that include the first heart sounds (S1) are aligned 502 based on the onset of the first heart sounds (S1). These segments also include the preceding fourth heart sounds (S4). In one embodiment, the alignment is based on a rough alignment involving a cross-correlation for each heart beat to estimate the lag to all other beats, and a shifting of each beat according to a mean of the lags to the other sounds. It is further based on a fine alignment involving a cross-correlation of each heart beat to the median beat and a shifting of each heart beat according to the lags to the median beat.

Figure 7:
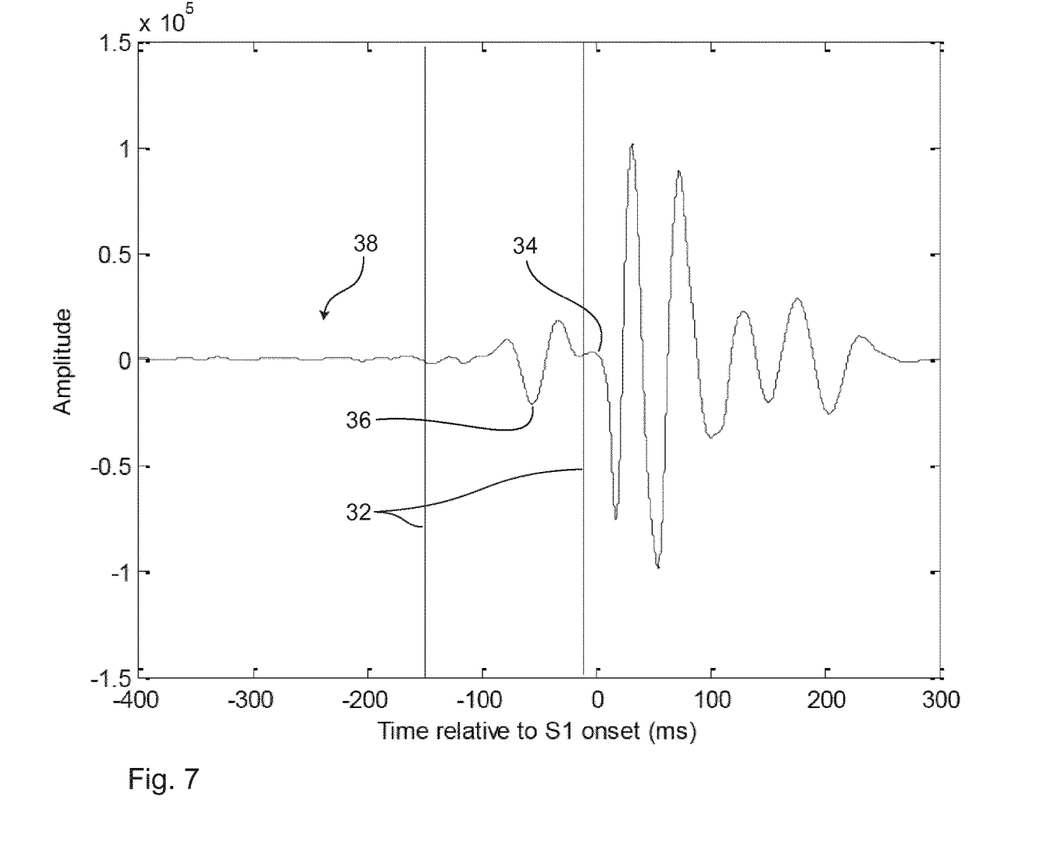
FIG. 7 is graph showing an example of a typical mean segment.

A mean segment is calculated 504 based on the aligned segments. The position in time of the first heart sound (S1) in the mean segment is then determined 508, which is the onset of the first heart sound (S1) that is effectively known from the alignment as such. A fourth heart sound period in the mean segment is determined 510 as the period that starts at 120 milliseconds before the position in time of the first heart sound (S1) and ends 15 milliseconds before the position in time of the first heart sound (S1). The amplitude of the fourth heart sound (S4Amp) is then determined 512 based on the peak amplitude of fourth heart sound period. This means effectively that the amplitude of the fourth heart sound (S4Amp) has been determined 506 based on the energy of the fourth heart sound (S4) in the mean segment, since the energy relates to the amplitude. A fourth heart sound period 32, an onset 34 of the first heart sound (S1), and a peak amplitude 36 of a fourth heart sound (S4) are indicated in a mean segment 38 shown in FIG. 7.

Figure 6A:
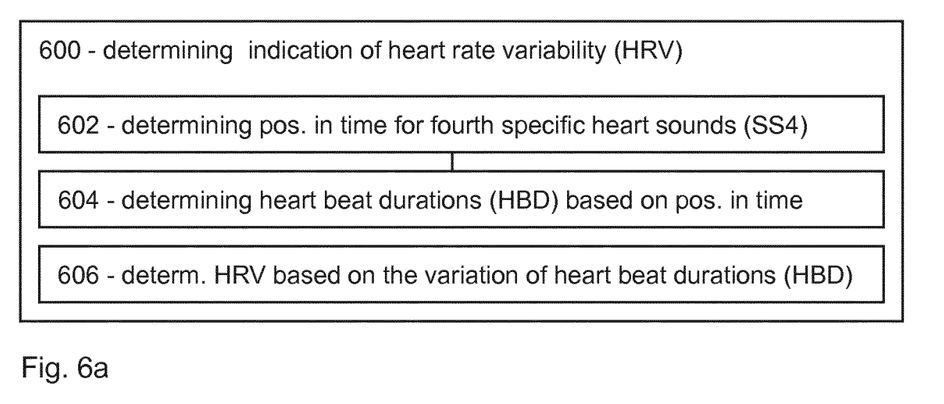
FIG. 6a is a schematic flowchart illustrating an embodiment of a step for determining an indication of a heart rate variability (HRV)

In the next step of the method an indication of a heart rate variability (HRV) is determined 600, which is illustrated in detail in FIG. 6a. The plurality of heart sounds (S) contains a plurality of fourth specific heart sounds (SS4) in the form of first heart sounds (S1) generated by mitral valve closures (MC). The position in time of each first heart sounds (S1) is determined as the onset of the first heart sounds (S1). A plurality of heart beat durations (HBD) is determined as the duration between the positions in time of consecutive first heart sounds (S1). The indication of the heart rate variability (HRV) is then determined 606 as the standard deviation of the remaining heart beat durations (HBD). This means effectively that the indication of a heart rate variability (HRV) has been determined based on the plurality of heart sounds (S).

Figure 6B:
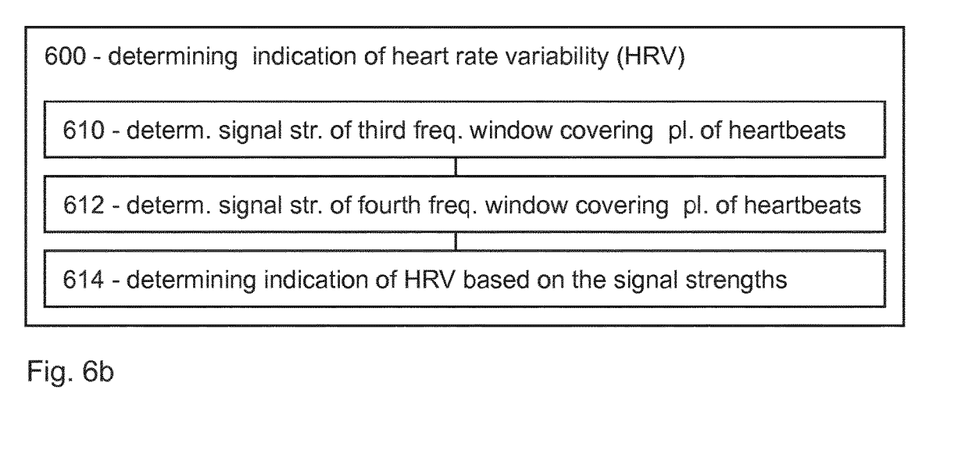
FIG. 6b is a schematic flowchart illustrating an alternative embodiment of a step for determining an indication of a heart rate variability (HRV)

An alternative embodiment the step of determining 600 of the heart rate variability (HRV) is illustrated in FIG. 6b. The energy in a third frequency window ranging from 0.003 Hz to 0.04 Hz in a period of the sound recording covering more than 60 heartbeats is determined 610. In one embodiment the third frequency window ranges from 0.04 Hz to 0.15 Hz. Additionally, the energy in a fourth frequency window ranging from 0.15 Hz to 0.4 Hz in the same period is determined 612.

In one embodiment, the above is achieved by resampling the period so that the separation between all neighboring first heart sounds (S1) of the heartbeats, obtained from the plurality of heart sounds (S), is the same and by producing a frequency power spectrum by a Fourier transform of the resampled period. The energy between 0.003 Hz and 0.04 Hz, and between 0.15 Hz to 0.4 Hz is then determined from the frequency power spectrum. An indication of the heart rate variability (HRV) is then determined 614 as the ratio between the energy of the 0.003 Hz to 0.04 Hz frequency window over the 0.15 Hz to 0.4 Hz frequency window. Effectively, this means that that the indication of the heart rate variability (HRV) is determined 614 based on the signal strengths of the third frequency window and the fourth frequency window, and that it is determined 600 based on the plurality of heart sounds (S).

In the next step of the method the indication of the risk for coronary artery disease (CAD) is determined 700 based on the determined frequency power measure (FPM), the determined amplitude of the fourth heart sound (S4Amp), and the determined indication of the heart rate variability (HRV). This is achieved employing the determined measures in a trained linear discriminate analysis (LDA).

Proof of Concept

An embodiment of the proposed technology was employed in a study involving 722 non-CAD subjects and 153 CAD subjects. A receiving operating curve (ROC) was generated and the area under the curve (AUC) was determined. The results are presented in Table 1 and indicate that the heart rate variability (HRV) improves the area under the curve (AUC) by about 1.1%. It can be concluded that the heart rate variability (HRV) has a significant classification performance in the acoustic score achieved by the proposed technology. It is envisioned that the classification performance would be improved if further acoustic derived measures are used.

TABLE 1

|  | AUC value FPM + S4Amp + HRV | AUC value FPM + S4Amp |
|---|---|---|
| Acoustic score | 62.5% | 60.4% |
| Clinical score | 79.2% | 79.1% |

The invention claimed is:

1. A method performed by an electronic stethoscope or a system for indicating a risk for coronary artery disease (CAD) for a person, the method comprising:
   obtaining a sound recording covering a plurality of heartbeats from a microphone placed on the person's chest;
   identifying a plurality of heart sounds in the sound recording;
   obtaining a plurality of segments from the sound recording based on the plurality of heart sounds, wherein each segment covers at least a portion of a heart cycle including a diastole;
   determining a frequency power measure (FPM) based on a signal strength of a first frequency window of a period in the diastole of a first number of segments of the plurality of segments, and a signal strength of a second frequency window of the period in the diastole, wherein the second frequency window has a low cutoff that is above a high cutoff of the first frequency window, wherein determining the FPM comprises (1) determining a first sum based on the sum of the energy in the first frequency window of the first number of segments; (2) determining a second sum based on the sum of the energy in the second frequency window of the first number of segments; and (3) determining the FPM based on one of a ratio (FPR) between the first sum and the second sum, and the relative magnitude of the first sum and the second sum;

determining an amplitude of a fourth heart sound (S4Amp) based on the plurality of heart sounds and the plurality of segments;

determining an indication of a heart rate variability (HRV) based on the plurality of heart sounds; and determining the indication of the risk for coronary artery disease (CAD) based on the frequency power measure (FPM), the amplitude of the fourth heart sound (S4Amp), and the indication of the heart rate variability (HRV).

2. The method according to claim 1, wherein the first frequency window has a low cutoff in the range 20-40 Hz and a high cutoff in the range 80-100 Hz, and wherein the second frequency window has a low cutoff in the range 180-220 Hz and a high cutoff in the range 250-800 Hz.

3. The method according to claim 1, wherein the plurality of heart sounds comprises a plurality of second specific heart sounds (SS2), and wherein determining a frequency power measure (FPM) comprises:

determining a position in time of the period in the diastole of each of the first number of segments relative to the second specific heart sound (SS2) in each segment, wherein the second specific heart sound (SS2) is a second heart sound (S2) relating to an aortic valve closure (AC), wherein the position in time of the second heart sound (S2) corresponds to either an onset or a peak of the of the second heart sound (S2), and wherein determining the position in time of the period comprises:

determining the position in time of the second heart sound (S2) in each of the first number of segments; and determining the period in the diastole in each segment as a period that starts later than 160-190 milliseconds after the position in time of the second heart sound (S2) of the segment, and ends before 430-470 milliseconds after to the position in time of the second heart sound (S2) of the segment.

4. The method according to claim 1, wherein the plurality of heart sounds comprises a plurality of third specific heart sounds (SS3), and wherein determining the amplitude of the fourth heart sound (S4Amp) comprises:

aligning a second number of segments of the plurality of segments based on the plurality of third specific heart sounds (SS3);

calculating a mean segment based on the aligned second number of segments; and determining the amplitude of the fourth heart sound (S4Amp) based on the energy of the fourth heart sound (S4) in the mean segment.

5. The method according to claim 4, wherein the third specific heart sound (SS3) is a first heart sound (S1) relating to mitral valve closure (MC), and wherein determining the amplitude of the fourth heart sound (S4Amp) comprises:

determining the position in time of the first heart sound (S1) in the mean segment;

determining a fourth heart sound (S4) period in the mean segment that starts in the range 100-140 milliseconds before the position in time of the first heart sound (S1) and ends in the range 20-10 milliseconds before the position in time of the first heart sound (S1); and determining the amplitude of the fourth heart sound (S4Amp) based on the energy of the fourth heart sound (S4) period;

wherein the position in time of the first heart sound (S1) corresponds to either the onset or the peak of the of the first heart sound (S1).

6. The method according to claim 1, wherein determining the indication of the heart rate variability (HRV) comprises:

determining the positions in time for a plurality of fourth specific heart sounds (SS4) of the plurality of heart sounds (S);

determining a plurality of heartbeat durations (HBD), wherein each heartbeat duration (HBD) is the time between the positions in time of two consecutive fourth specific heart sounds (SS4); and determining the indication of the heart rate variability (HRV) based on the variation of the plurality of heartbeat durations (HBD).

7. The method according to claim 6, wherein the position in time of a fourth specific heart sound (SS4) of the plurality of fourth specific heart sounds (SS4) corresponds to either the onset or the peak of the fourth specific heart sound (SS4).

8. The method according to claim 6, wherein each of the plurality of fourth specific heart sounds (SS4) is the first heart sound (S1) relating to a mitral valve closure (MC).

9. The method according to claim 1, wherein determining the indication of the heart rate variability (HRV) comprises:

determining the signal strength of a third frequency window of a period of the sound recording covering at least a portion of the plurality of heartbeats, wherein the third frequency window has a high cutoff that is below 2 Hz; and determining the indication of the heart rate variability (HRV) based on the signal strength of the third frequency window;

wherein the third frequency window has a low cutoff that is above 0.001 Hz.

10. The method according to claim 9, wherein the third frequency window has a low cutoff in the range 0.001-0.005 Hz and a high cutoff in the range 0.02-0.06 Hz.

11. The method according to claim 9, wherein the third frequency window has a low cutoff in the range 0.02-0.06 Hz and a high cutoff in the range 0.1-0.2 Hz.

12. The method according to claim 9, wherein the third frequency window has a low cutoff in the range 0.1-0.2 Hz and a high cutoff in the range 0.3-0.5 Hz.

13. The method according to claim 9, wherein determining the indication of the heart rate variability (HRV) comprises:

determining the signal strength of a fourth frequency window of the period of the sound recording, wherein the fourth frequency window that has a high cutoff below 2 Hz, and that no more than partly overlaps the third frequency window; and determining the indication of the heart rate variability further based on the signal strength of the fourth frequency window;

wherein the fourth frequency window has a low cutoff that is above 0.001 Hz.

14. The method according to claim 1, wherein determining an indication of the risk for coronary artery disease (CAD) is further based on a trained linear discriminate analysis (LDA) involving the frequency power measure (FPM), the amplitude of the fourth heart sound (S4Amp), and the indication of the heart rate variability (HRV).

15. A system for indicating a risk for coronary artery disease (CAD) for a person, wherein the system comprises:
   a microphone configured for obtaining a recording of heart sounds from the person's heart when placed on the person's chest; and
   a processor operatively connected to the microphone and configured, when programmed by executable instructions, to:
   (a) identify a plurality of heart sounds in the recording of heart sounds;
   (b) obtain a plurality of segments from the recording of heart sounds based on the plurality of heart sounds, wherein each segment covers at least a portion of a heart cycle including a diastole;
   (c) determine a frequency power measure (FPM) based on a signal strength of a first frequency window of a period in the diastole of a first number of segments of the plurality of segments, and a signal strength of a second frequency window of the period in the diastole, wherein the second frequency window has a low cutoff that is above a high cutoff of the first frequency window, wherein the FPM is determined by: (1) determining a first sum based on the sum of the energy in the first frequency window of the first number of segments; (2) determining a second sum based on the sum of the energy in the second frequency window of the first number of segments; and (3) determining the frequency power measure (FPM) based on one of a ratio (FPR) between the first sum and the second sum, and the relative magnitude of the first sum and the second sum;
   (d) determine an amplitude of a fourth heart sound (S4Amp) based on the plurality of heart sounds and the plurality of segments;
   (e) determine an indication of a heart rate variability (HRV) based on the plurality of heart sounds; and
   (f) determine an indication of the risk for coronary artery disease (CAD) based on the frequency power measure (FPM), the amplitude of the fourth heart sound (S4Amp), and the indication of the heart rate variability (HRV).

16. The system according to claim 15, wherein determining the indication of the heart rate variability (HRV) comprises:
   determining the signal strength of a third frequency window of a period of the recording of heart sounds covering at least a portion of the plurality of heartbeats, wherein the third frequency window has a high cutoff that is below 2 Hz; and
   determining the indication of the heart rate variability (HRV) based on the signal strength of the third frequency window;
   wherein the third frequency window has a low cutoff that is above 0.001 Hz.

17. A computer program product for use in a system comprising a microphone configured to be placed on a person's chest for obtaining a recording of heart sounds from the patient's heart, and a processor operatively connected to the microphone, wherein the computer program product comprises program code instructions configured, when executed by the processor of the system, to cause the processor to perform a method comprising the steps of:
   (a) identifying a plurality of heart sounds in the recording of heart sounds;
   (b) obtaining a plurality of segments from the recording of heart sounds based on the plurality of heart sounds, wherein each segment covers at least a portion of a heart cycle including a diastole;
   (c) determining a frequency power measure (FPM) based on a signal strength of a first frequency window of a period in the diastole of a first number of segments of the plurality of segments, and a signal strength of a second frequency window of the period in the diastole, wherein the second frequency window has a low cutoff that is above a high cutoff of the first frequency window, wherein determining the FPM comprises (1) determining a first sum based on the sum of the energy in the first frequency window of the first number of segments; (2) determining a second sum based on the sum of the energy in the second frequency window of the first number of segments; and (3) determining the FPM based on one of a ratio (FPR) between the first sum and the second sum, and the relative magnitude of the first sum and the second sum;
   (d) determining an amplitude of a fourth heart sound (S4Amp) based on the plurality of heart sounds and the plurality of segments;
   (e) determining an indication of a heart rate variability (HRV) based on the plurality of heart sounds; and
   (f) determining an indication of a risk for coronary artery disease (CAD) based on the frequency power measure (FPM), the amplitude of the fourth heart sound (S4Amp), and the indication of the heart rate variability (HRV).

18. The computer program product according to claim 17, wherein determining the indication of the heart rate variability (HRV) comprises:
   determining the signal strength of a third frequency window of a period of the recording of heart sounds covering at least a portion of the plurality of heartbeats, wherein the third frequency window has a high cutoff that is below 2 Hz; and
   determining the indication of the heart rate variability (HRV) based on the signal strength of the third frequency window;
   wherein the third frequency window has a low cutoff that is above 0.001 Hz.

* * * * *